United States Patent [19]
Christy

[11] Patent Number: 5,776,148
[45] Date of Patent: *Jul. 7, 1998

[54] SURGICAL STAB WOUND CLOSURE DEVICE AND METHOD

[76] Inventor: William J. Christy, 1324 Sunset Dr., Winter Park, Fla. 32789

[*] Notice: The term of this patent shall not extend beyond the expiration date of Pat. No. 5,503,634.

[21] Appl. No.: 592,875

[22] Filed: Jan. 24, 1996

Related U.S. Application Data

[63] Continuation of Ser. No. 127,775, Sep. 27, 1993, Pat. No. 5,503,634, which is a continuation-in-part of Ser. No. 54,856, Apr. 28, 1993, Pat. No. 5,350,385.

[51] Int. Cl.$^6$ ................................................. A61B 17/00
[52] U.S. Cl. ........................... 606/144; 606/139; 606/223
[58] Field of Search ................................ 606/139, 144, 606/145, 147, 148, 222, 223, 205, 207; 223/102–104; 604/167, 246, 247, 256, 264, 280, 283, 164, 169

[56] References Cited

U.S. PATENT DOCUMENTS

| 5,304,184 | 4/1994 | Hathaway et al. | 606/148 |
| 5,364,408 | 11/1994 | Gordon | 606/144 |
| 5,522,846 | 6/1996 | Bonutti | 606/139 |

Primary Examiner—Jeffrey A. Schmidt
Attorney, Agent, or Firm—Allen, Dyer, Doppelt, Milbrath & Gilchrist, P.A.

[57] ABSTRACT

A device for the surgical suturing of narrow incisions that penetrate through a plurality of tissue layers includes a needle having the shape of an elongated "J." The device further includes a slidable locking member that serves the dual purpose of blocking the tip of the suture needle and also of preventing gas leakage out of the body cavity during the suturing procedure in order to maintain pneumoperitoneum.

1 Claim, 10 Drawing Sheets

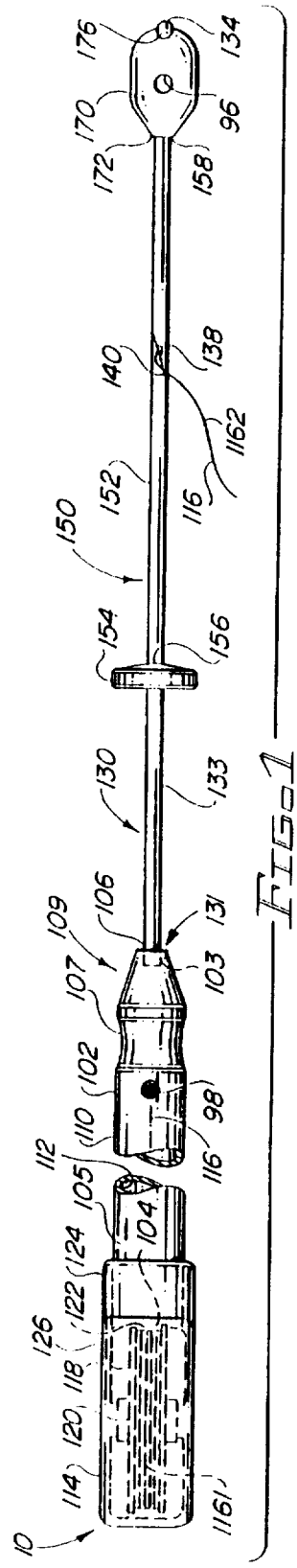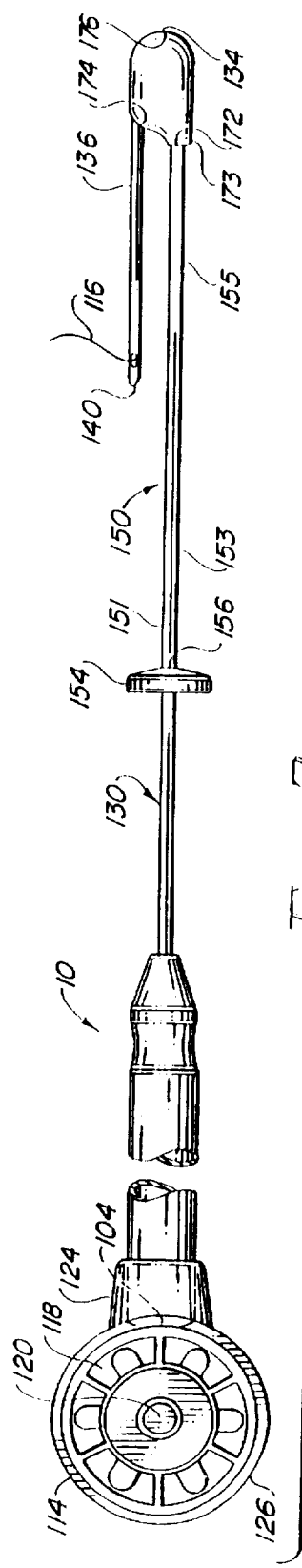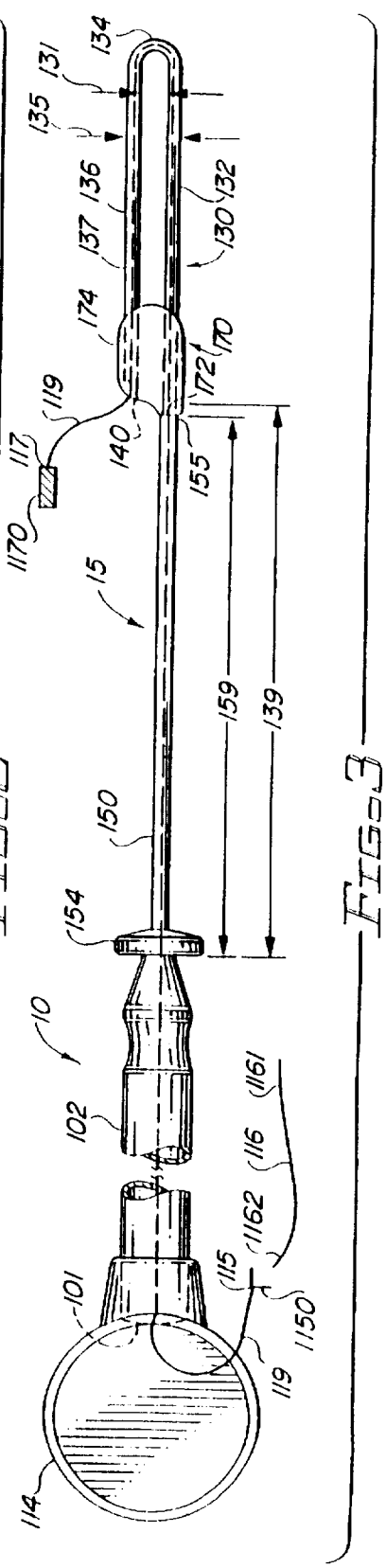

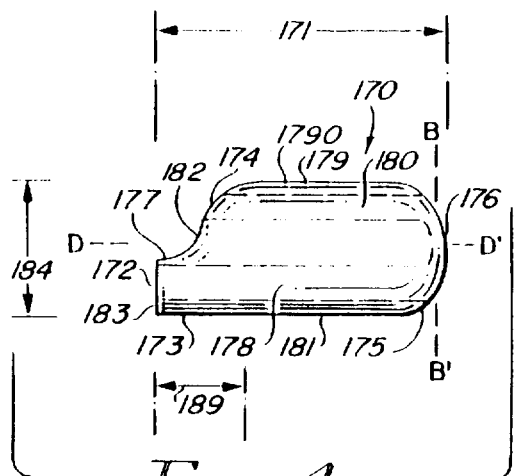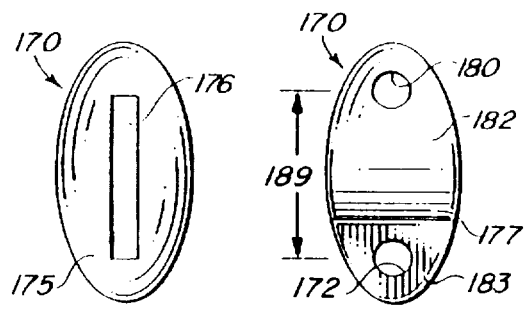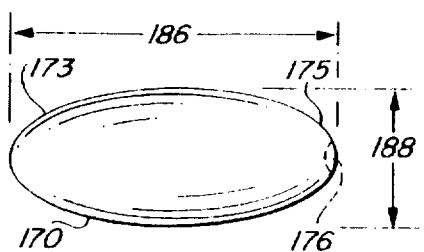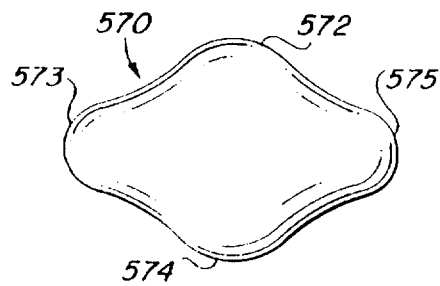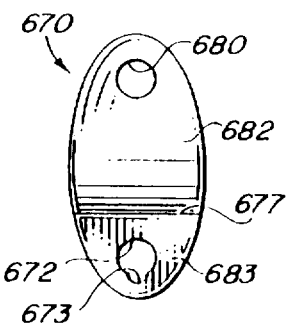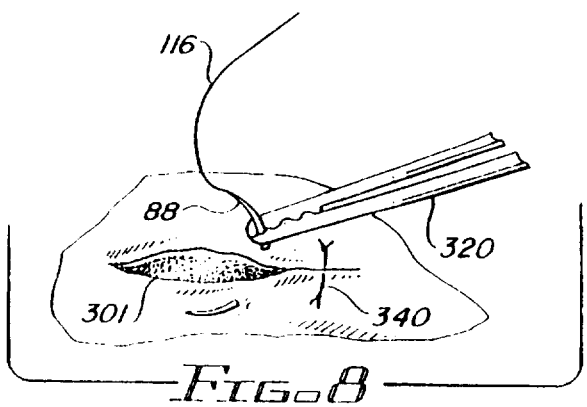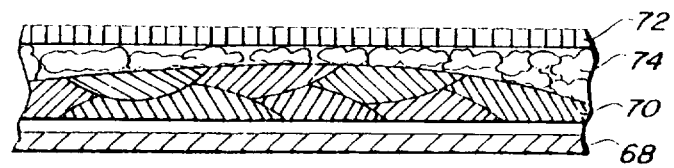

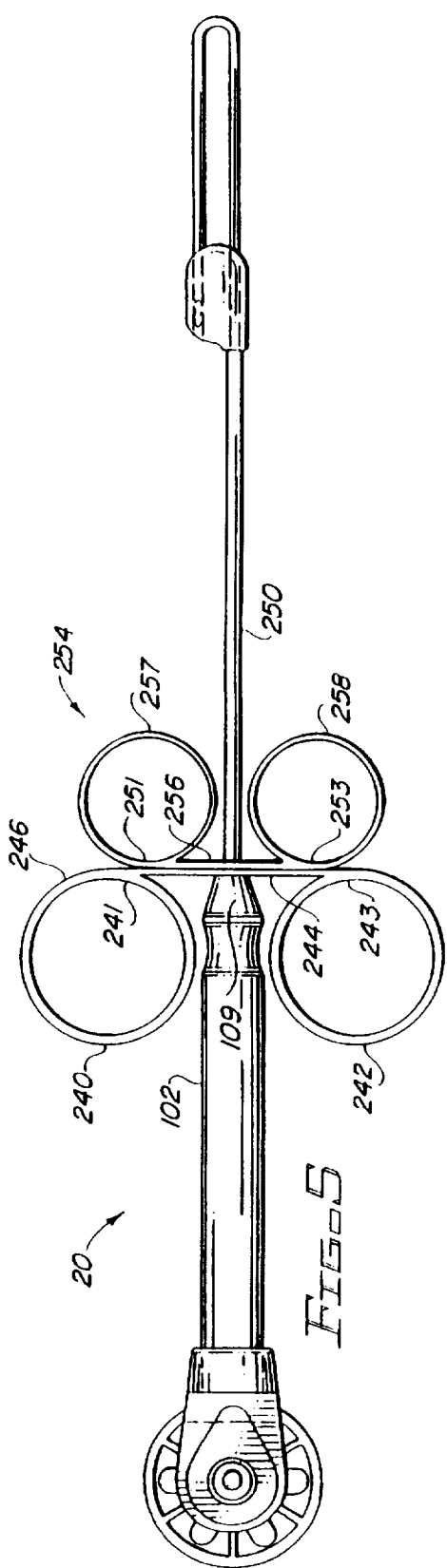
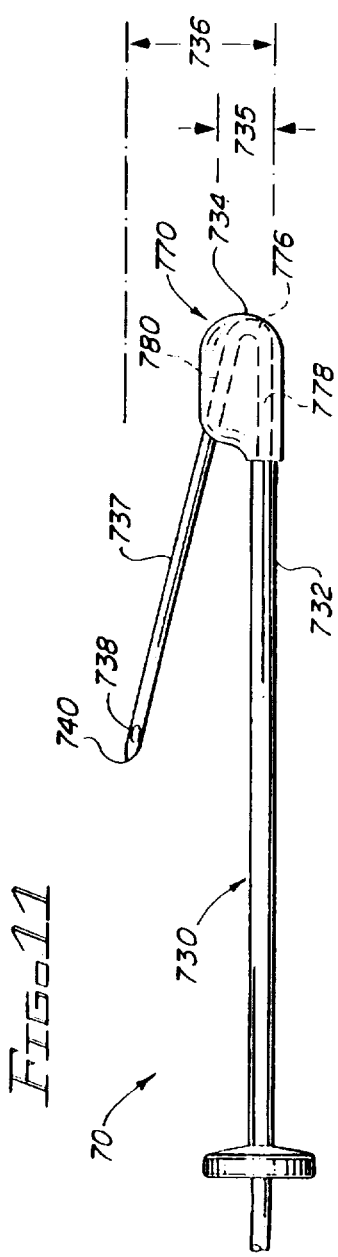

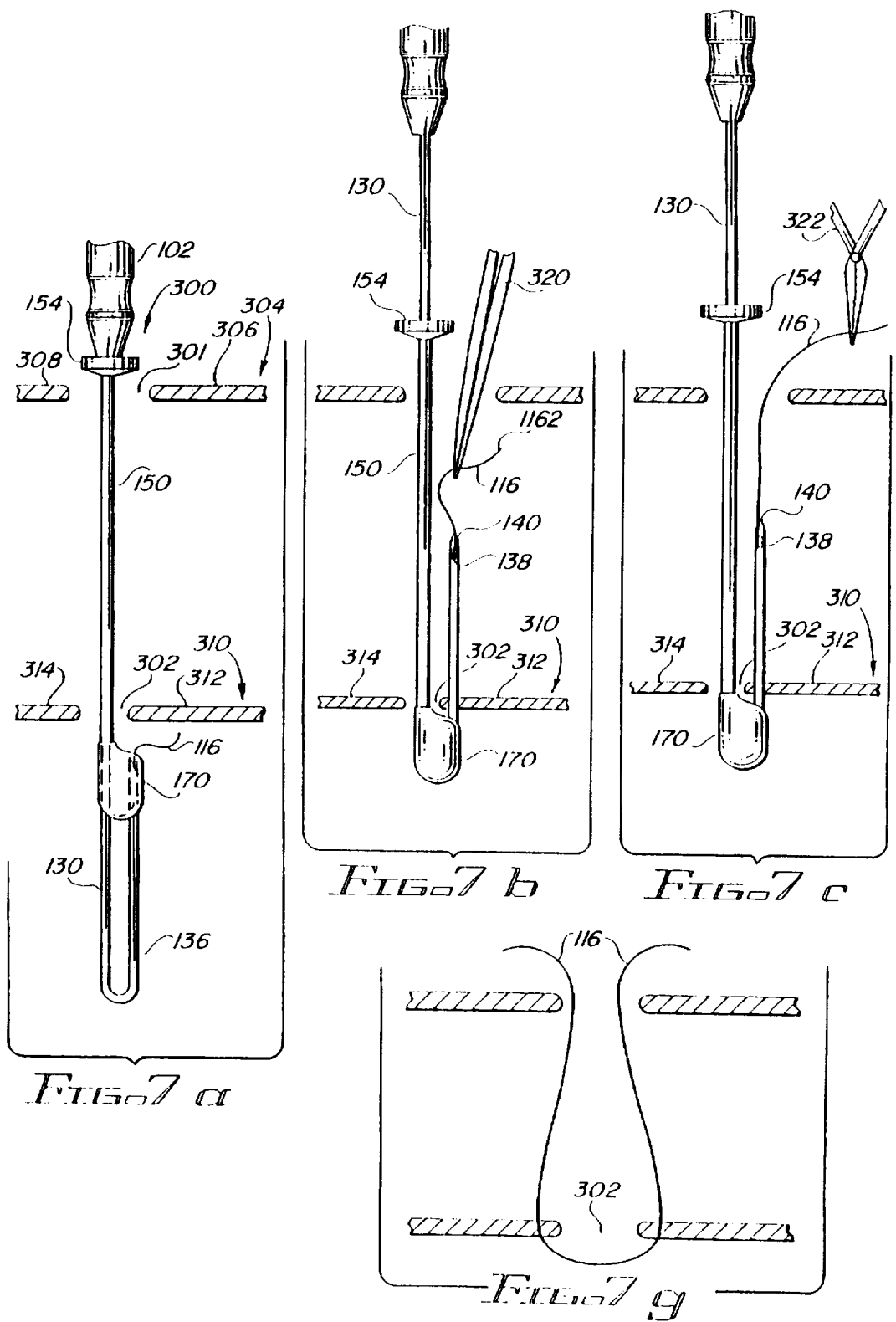

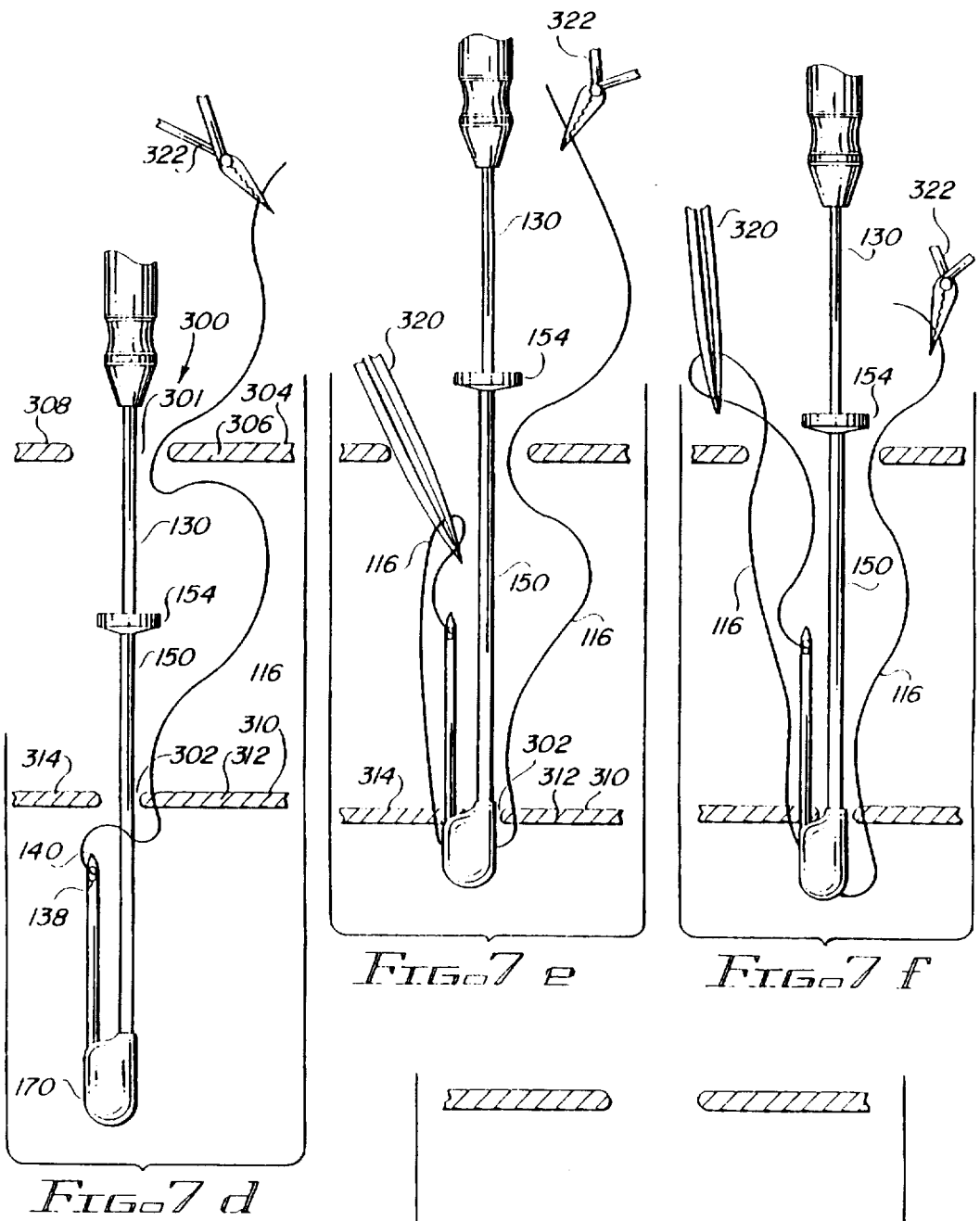

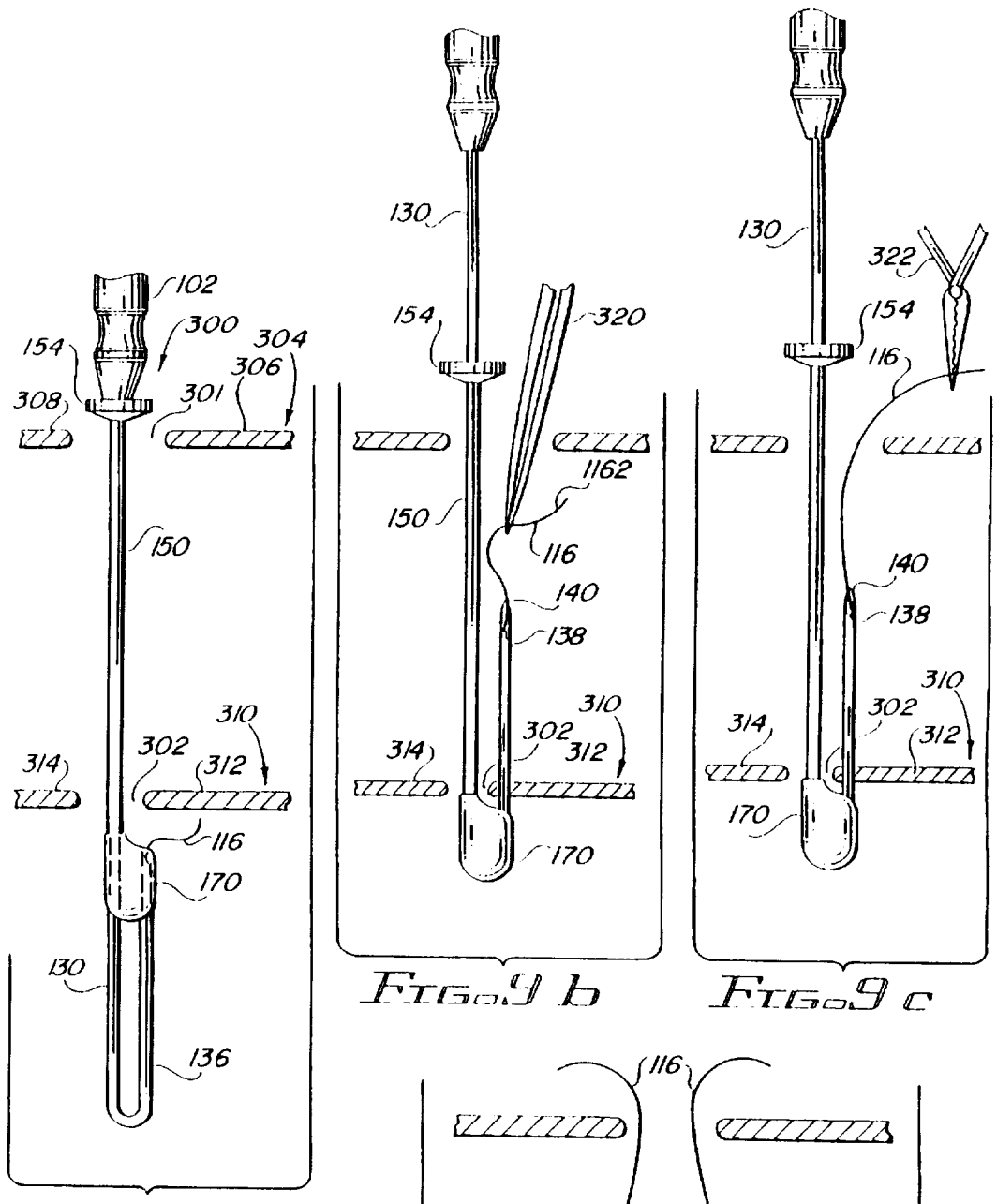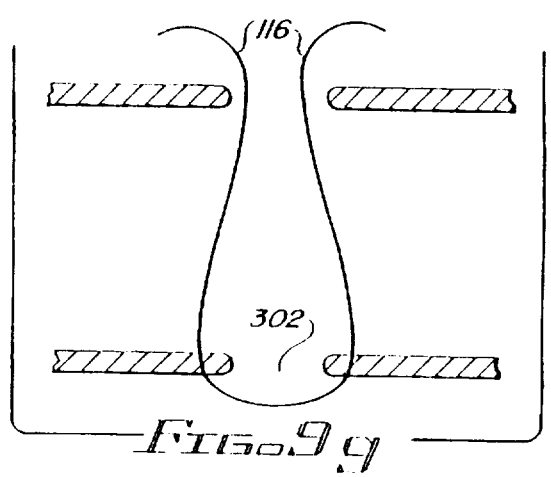

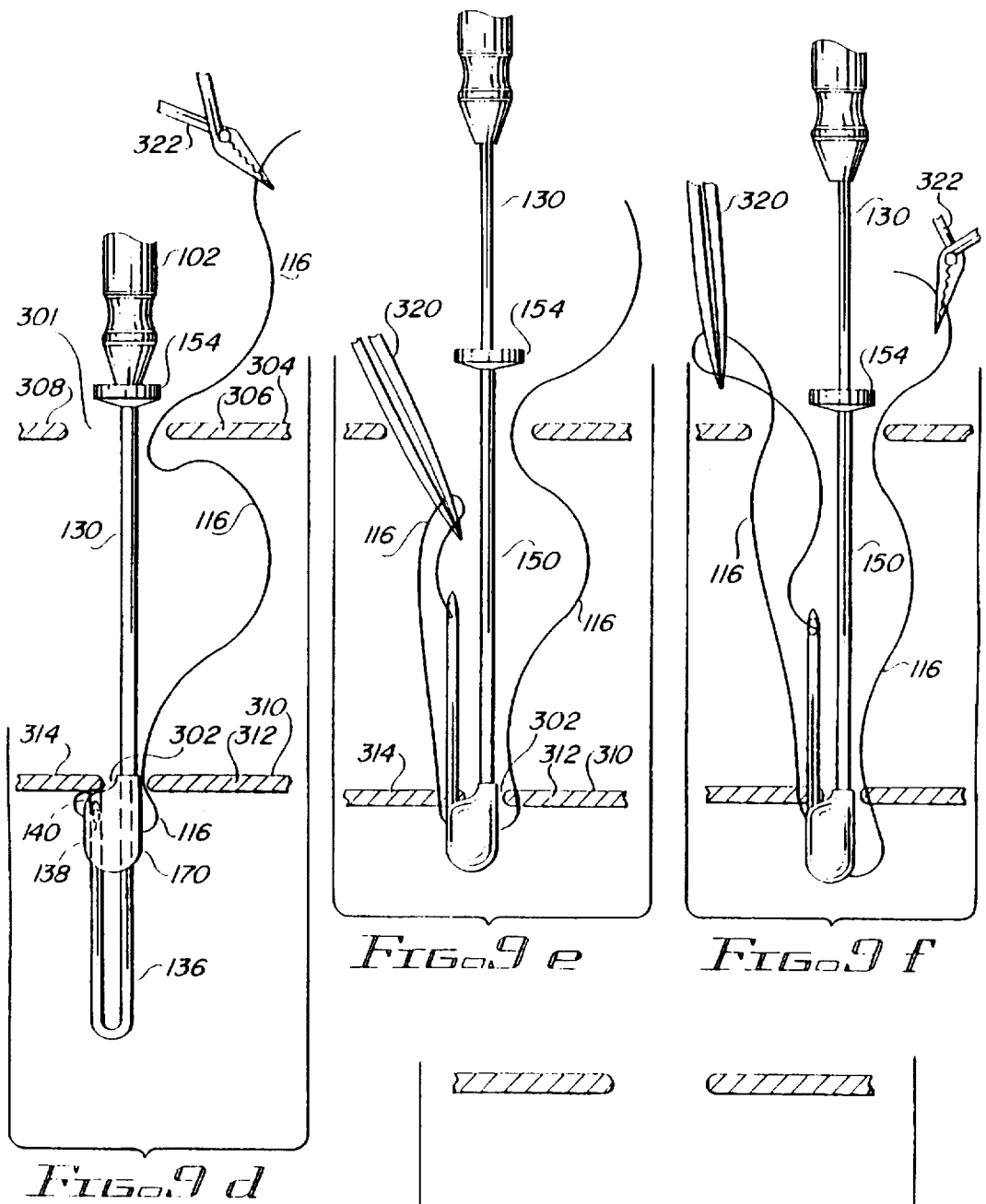

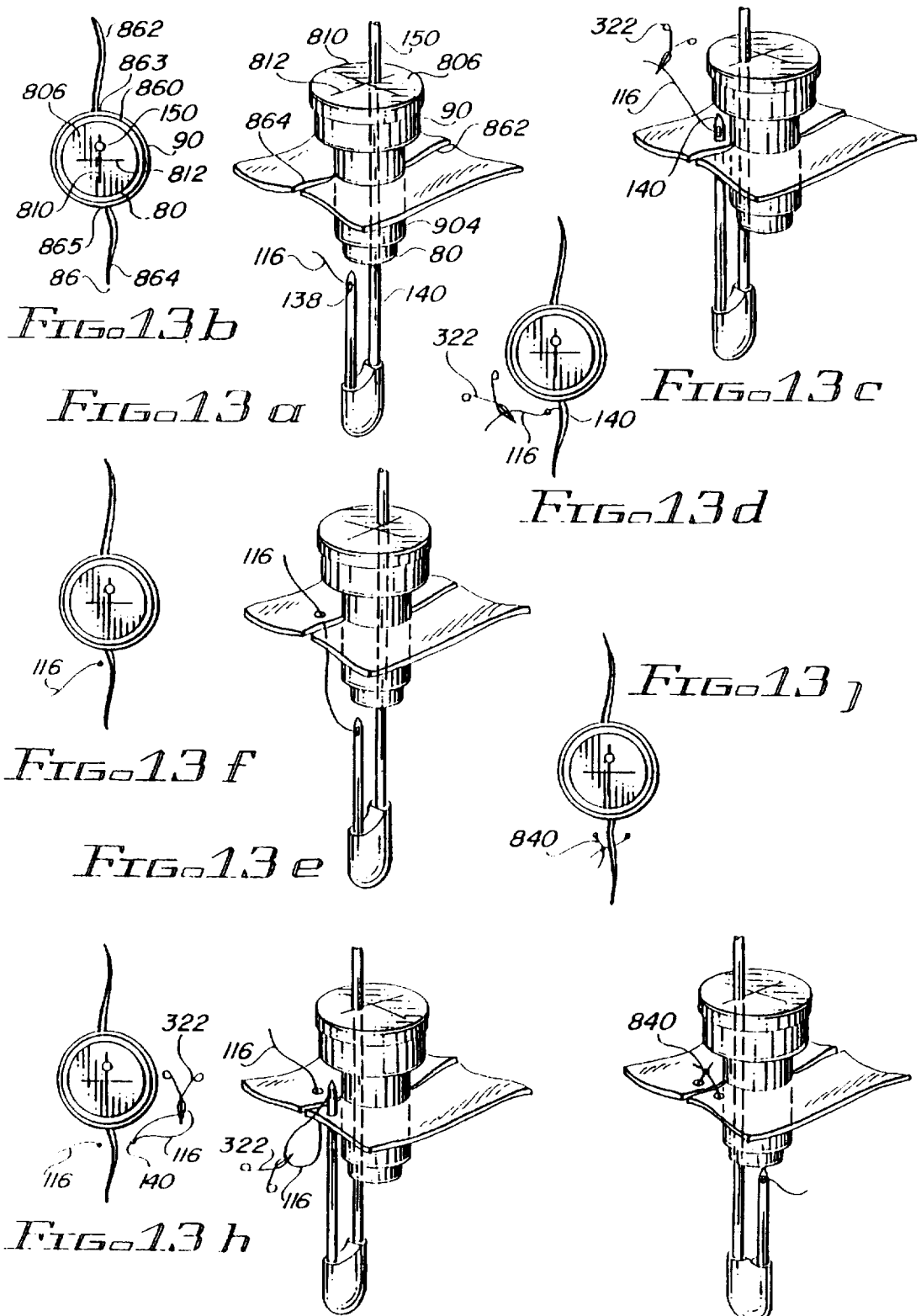

SURGICAL STAB WOUND CLOSURE DEVICE AND METHOD

This application is a continuation of application Ser. No. 08/127,775, "Surgical Stab Wound Closure Device and Method," filed on Sep. 27, 1993, U.S. Pat. No. 5,503,634, which is a continuation-in-part of application Ser. No. 08/054,856, "Surgical Stab Wound Closure Device and Method," filed in Apr. 28, 1993, now issued U.S. Pat. No. 5,350,385.

BACKGROUND OF THE INVENTION

1. Field of the Invention

This invention relates generally to the field of surgical devices and, more particularly, to surgical suturing apparati and methods of surgical suturing, specifically in laparoscopic and endoscopic applications.

2. Description of Related Art

Laparoscopic or endoscopic surgical procedures are now widely used in many specialties in the surgical community. These procedures generally involve a "C"-shaped incision through the navel, through skin, adipose tissue, fascia, muscle, and peritoneum, which comprise the abdominal wall or thoracic wall. Using this method many organs of the gut may be viewed and operated upon: gall bladder, intestines, appendix, uterus, fallopian tubes, ovaries, and lungs.

Trocars, pointed cannulae with pointed obturators for piercing the wall of a cavity, are often used to create ports through which surgical instruments may be passed, instead of making long incisions in the abdominal or thoracic wall. The diameter of the trocar differs based upon the procedure to be performed, and may range from 3 to 33 millimeters.

Multiple trocars may be used so that a variety of instruments may be used simultaneously, such as a camera or magnifying lens, cutting, ligating, grasping, or suturing apparati. In this way, for example, forceps passed through one trocar can grasp tissue while a cutting operation is performed through another, the whole procedure being visualized on a screen connected to a camera inserted into the cavity through a third trocar.

Such microsurgery techniques have made it necessary to perform wound closure on a much smaller scale than was required by the previously used large incisions. Up until now, multiple-layer closure has been utilized, whereby the entire abdominal wall has been sutured together to prevent evisceration or herniation of internal organs through the incision site. Should only the skin tissue be closed, complications can occur that include the viscera pushing up through the tissue. The tissue strangulates an organ that may get pushed up causing infection, peritonitis and possibly death.

Laparoscopic or endoscopic procedures generally entail the introduction of elevated-pressure gas into the body cavity being operated upon. This enables the surgeon visualize the area better and also provides additional room in which to work. Significant leakage of gas pressure would cause the area to collapse, disturbing and delaying the procedure, which could be dangerous. Such a leakage can occur, for instance, during suturing, after a trocar has been removed.

The laparoscopic or endoscopic procedures addressed herein typically entail a plurality of incisions, as mentioned. A problem that may occur is the suturing of the last subcutaneous incision, since that is likely to be the incision for the trocar through which visualizing means have been inserted. Thus the final incision must be sutured "blind."

A further difficulty that may be encountered in surgery employing trocars is that during the insertion of the trocar a blood vessel may be inadvertently sectioned. The bleeding resulting from such a puncture is difficult to control, as the wall of the trocar blocks the severed ends of the vessel, making it difficult to repair.

Surgical suturing instruments have been the subject of prior references. King (U.S. Pat. No. 373,372, issued Nov. 15, 1887), McBrayer (U.S. Pat. No. 389,235, issued Sep. 11, 1888), and Violante (U.S. Pat. No. 3,840,017, issued Oct. 8, 1974) disclose curved, hollow suture needles with suture thread positioned in and emerging from the bore and having a storage means for suture thread located within or upon a handle into which the suture needle is affixed. Violante's device further comprises a sharpened and beveled tip capable of cutting the suture thread when the procedure is completed. Karle (U.S. Pat. No. 2,327,353, issued Dec. 12, 1940) described a device for surface wound stitching that utilizes two spools of suture thread for creating a lock stitch, not unlike that produced by a conventional sewing machine having a threaded needle that communicates with another spool of thread, the bobbin.

Baber's invention (U.S. Pat. No. 5,152,769, issued Oct. 6, 1992) is specifically directed to a suture needle for laparoscopic procedures. His apparatus is designed for use with a trocar, and comprises a pair of concentric and slidable barrel portions. To the outer barrel is affixed a hollow suture needle having a curved tip and a hole through which suture thread may pass. A hook-shaped member is affixed to the inner barrel. Suturing is then accomplished by rotating the outer barrel to guide the needle through the tissue to be stitched and grasping the suture thread with the hook-shaped member to form a loop, which is held in place within the inner barrel until the next suture is made.

SUMMARY OF THE PRESENT INVENTION

The Surgical Suturing Apparatus

The surgical suturing apparatus of the present invention is directed to closing incisions penetrating a plurality of layers of tissue, particularly narrow incisions such as stab wounds or those formed by trocar punctures.

This device comprises a tubular body, dimensioned to fit into a human hand, in one embodiment having one or more depressions for finger positioning. Suture thread holding means are positioned at the proximal end of the tubular body, and may consist of a rotatable spool, upon which suture material is wound.

Onto the distal end of the tubular body is affixed a suture needle having a bore sufficiently large to permit suture material to pass therethrough, the suture needle in the shape of a "deep J," comprising a first, proximal end and a second, distal end and with a first and a second substantially parallel straight section each adjacent a corresponding one of the ends with a curved middle section between the first and the second straight sections, the distal end forming a generally "U" shape, the second straight section adjacent the distal end having a pointed tip. The first and second straight sections may be provided having different dimensions for a variety of surgical procedures. A gate communicating with the suture needle bore is placed along the second straight portion of the suture needle, away from the pointed tip.

It can be seen that the most distal portion of the suture needle of the present invention, that is, the bottom of the "U," is the first section of the device to enter the incision. The thin and rounded nature of this portion enables suture needle entry that is not only easy to effect, but also causes no further tissue damage. Prior art suturing devices, which have at their distal end a pointed structure, can be difficult to insert and can tear tissue adjacent the incision while the surgeon is searching for the exact site to be sutured.

The suture material is threaded from the suture thread holding means through, sequentially, a hole in the proximal end of the tubular body, the tubular body, a hole in the distal end of the tubular body, the bore of the suture needle, and the suture gate.

The apparatus is further provided with a suture locking means, comprising a tubular sheath and a locking member. The tubular sheath, which is dimensioned to slidably surround the first straight section of the suture needle, has a proximal end, a distal end, and a bore. The length of the tubular sheath is determined by the distance between the first end of the tubular body and the pointed tip of the suture needle. The bore is smaller than the first end of the tubular body, so that the tubular sheath's movement is stopped in the proximal direction by the tubular body.

The locking member of the suture locking means will be seen to serve both to clamp the suture material at the suture gate and also to plug an incision, thereby maintaining gas pressure inside the body cavity being sutured. The locking member comprises a proximal end, a distal end, a first and a second bore, and is affixed at its proximal end to the distal end of the tubular sheath. The first bore surrounds and slidably engages the first straight section of the suture needle; the second bore surrounds and slidably engages the second straight section of the suture needle.

While the first and the second bore are substantially parallel in one embodiment, it is also possible to construct the second bore at a small angle to the first bore, in order to effect a small angle of the first section to the second section of the suture needle. This small angle would cause the distance between the first and second straight sections of the suture needle to be greater at the proximal than at the distal end. The purpose of this flaring will be discussed in the Method section.

Various geometries are provided for different embodiments of the locking member, as dictated by incision and/or trocar size. For small trocar sizes, the cross-sectional shape in the plane of the tissue is elliptical; for larger trocars, the shape has bulges along the long axis of the ellipse. These geometries, which can be seen by one skilled in the art to be but two of many possible ones, have been designed for their efficacy in incision blocking.

The tubular sheath is slidable along the first straight section of the suture needle, being capable of assuming a plurality of positions. The two extreme positions are defined by the respective lengths of the tubular sheath and the first straight section of the suture needle. When in the first position, the proximal end of the tubular sheath is adjacent the first end of the tubular body. In this first position the locking member covers the suture needle's pointed tip and suture gate. When in the second position, the tubular sheath is slid in the distal direction, placing the distal end of the locking member adjacent the curved middle section of the suture needle. In this second position the pointed tip and suture gate of the suture needle are exposed.

In a further embodiment, the locking member comprises a channel communicating with the second bore dimensioned to permit suture material to pass therethrough. In this embodiment suture material emerging from the suture gate lies within the channel when the locking member is in position to cover the suture gate.

In another embodiment the proximal end of the tubular sheath further comprises a grasping means, whereby the operator may more easily slide the tubular sheath along the suture needle.

In yet another embodiment the tubular sheath is spring loaded, enabling the operator to release the tubular sheath from the first position to the second position with release means. This embodiment permits one-handed operation.

In a still further embodiment the entire distal end of the device, including the suture needle, tubular sheath, and locking member, is enclosed within an air-tight enclosure, or cannula, so that gas pressure within the body cavity to be sutured is not compromised during the beginning of the suturing operation. The cannula has a gasket at both the distal and the proximal end, the gasket having two diametric slits at substantially right angles to each other, through which the suture needle and locking member may pass. The slits are dimensioned and the gasket material constructed so that a seal may be maintained as the tubular sheath and suture needle are moved in and out of the incision.

Another embodiment comprises the above-described enclosure system being itself enclosed in an air-tight manner within a trocar, again enabling the suturing operation to be carried out in a leakproof manner.

Method for Suturing Narrow Incisions

The method for utilizing the above-disclosed apparatus for suturing narrow incisions will now be described.

With the tubular sheath in the first position, that is, with the pointed tip and suture gate covered with the locking member, the distal end of the suture needle is inserted into the incision sufficiently deep that the pointed tip of the suture needle is beneath the deepest layer of tissue to be sutured. The tubular sheath is then slid into the second position, exposing the pointed tip and suture gate. The pointed tip is then brought surfaceward through a first side of the incision sufficiently far to pull the distal end of the suture material through a first side of the deepest layer of tissue to be sutured, penetrating only one layer of tissue.

Using forceps or other suture material grasping means, the suture material is brought out of the incision to a length sufficient for tying a knot and is then secured, for instance, with a clamping means such as a hemostat.

The suture needle is then pushed back into the incision, again sufficiently deep that the pointed tip is again beneath the deepest layer of tissue to be sutured. The suture needle is then rotated, so that the pointed tip is positioned beneath a second side of the incision, and then brought surfaceward once more, bringing the pointed tip and suture gate through the deepest layer of tissue to be sutured.

Using the forceps again, the suture material is grasped at the suture gate and pulled out of the incision to a length sufficient for tying a knot. The tubular sheath is returned to the first position, locking the suture material against the suture gate. The suture material is then cut at the point of being grasped by the forceps, the suture needle is withdrawn from the incision, and a knot is tied.

This procedure may be repeated on the same layer of tissue to form multiple sutures, such as in the form of an "X" or in a plurality of parallel sutures.

The procedure may also be repeated on successively more shallow layers of tissue until all but the cutaneous layer are closed, the final step of the closure comprising suturing the cutaneous layer by conventional means.

Utilizing the suture device embodiment in which the second straight section of the needle is flared, the surgeon is capable of piercing the tissue further away from the incision, thus enabling a wider suture. This technique may be desirable in some cases to ensure the strength of the suture.

Method for Suturing Narrow Incisions while Maintaining Gas Pressure within a Body Cavity As mentioned in the Background section, certain types of surgery are performed within body cavities that have been pressurized, essentially blowing up the area like a balloon. Obviously, in order to maintain this pressure, the area must be maintained as leakproof as possible. In the case of peritoneal surgery, for instance, in which carbon dioxide pressure is introduced to improve visualization of the operating site by the surgeon, the opening of an incision can cause loss of the pressure, collapsing the area being operated upon.

In one embodiment of the present invention, the surgical suturing apparatus described previously can also be utilized to maintain gas pressure within a body cavity during the suturing procedure. In this aspect the locking member serves to plug the subcutaneous puncture as well as to lock the suture material against the suture needle. Generally this method entails positioning the locking member in the subcutaneous incision and keeping it there throughout the suturing procedure by sliding the suture needle inside the tubular sheath. The suturing method used is identical to that described above except for this manipulation of the tubular sheath.

In a further embodiment the method of maintaining gas pressure may be carried out with the use of only one hand. This one-handed operation requires the spring-loaded apparatus described above.

In another embodiment, with the use of the device enclosed within a cannula, the suturing operation is performed utilizing the cannula as the means for maintaining gas pressure. In this method the suturing operation is performed with the distal end of the suture needle protruding from the distal end of the cannula. The cannula itself serves as the means for maintaining gas pressure during the suturing operation.

In yet another embodiment, the above method is utilized with the device embodiment having the cannula system sealingly attached to a trocar. Thus the trocar and cannula combination serve to maintain gas pressure during the suturing operation.

Method for Suturing a Plurality of Narrow Incisions

In laparoscopic procedures in which multiple incisions have been made, typically the last incision to be closed is that made for the trocar through which the visualizing means had been inserted. The problem addressed by the method presented here is that all but the last suturing operating can be carried out with the visualizing means still in place, and thus the last incision must be closed without the aid of the camera.

The method comprises the steps of closing all but two incisions, A and B, having a first and a second trocar, respectively, inserted therein. One of these incisions (A) is that into which the visualizing means is inserted. The surgeon then proceeds with the method for suturing incisions as described above on incision B, stopping, however, before tying the knot, and leaving the suture material outside the body cavity without tightening. The second trocar is left in incision B. The visualizing means is then removed from incision A and the first trocar, and it is then inserted into incision B through the second trocar. Next incision A is completely closed with the use of the method described above. It can be seen that the closing of incision A may be performed with the aid of the visualizing means, which now reside in incision B.

Next the trocar and visualizing means are removed from incision B, and a knot is tied in the suture material that had been left in place previously.

Thus all of the multiple incisions have been closed with the aid of the visualizing means.

Method for Suturing Blood Vessels Sectioned by Trocar Insertion

As mentioned in the Background section, the insertion of a trocar, which has a pointed tip, may itself cause damage by sectioning a blood vessel. The device of the present invention may be used to suture the severed ends of the damaged vessel while the trocar is in place, enabling the surgeon to control "bleeders."

The method for suturing severed blood vessels comprises the following steps: The distal end of the suture needle is inserted into the proximal end of the trocar sufficiently far that the distal end of the suture needle protrudes from the distal end of the trocar. The suture needle is then maneuvered so that the pointed tip is beneath the tissue layer that is immediately beneath the first end of the severed blood vessel. The second straight section of the suture needle is thereby positioned such that it is outside the imaginary cylinder formed by an extension in the distal direction of the trocar's distal end. The pointed tip is brought surfaceward, outside the trocar, through a first side of the tissue adjacent the first end of the blood vessel, and the suture material is grasped with grasping means such as forceps.

Next the distal end of the suture needle is reinserted into the incision. The pointed tip is next brought surfaceward, again outside the trocar, through a second side of the tissue adjacent the first end of the blood vessel, and the suture material is grasped with grasping means.

The suture material is then cut, and a knot is tied.

The same procedure is performed for the second end of the blood vessel, and thus both ends of the "bleeder" are closed.

OBJECTS OF THE INVENTION

It is thus an object of the present invention to provide a surgical suturing apparatus with which it is possible to suture at least one subcutaneous layer of tissue.

It is a further object to provide a surgical suturing apparatus with which it is possible to maintain gas pressure within a body cavity that is the operating field during the suturing procedure.

It is yet another object to provide a surgical suturing apparatus that may be utilized with one hand.

It is an additional object to provide a method of suturing at least one subcutaneous layer of tissue.

It is a further object to provide a method of suturing at least one subcutaneous layer of tissue of a body cavity while maintaining a desired gas pressure within that cavity.

It is yet another object to provide a one-handed method of suturing at least one subcutaneous layer of tissue.

It is an additional object to provide a method of suturing at least one subcutaneous layer of tissue in each one of a plurality of incisions.

It is a further object to provide a method of suturing blood vessels sectioned during the insertion of a trocar with the trocar in place.

BRIEF DESCRIPTION OF THE DRAWINGS

A preferred embodiment of the invention along with alternate embodiments are described by way of example with reference to the accompanying drawings, in which:

FIG. 1 illustrates the surgical suturing apparatus in front view, with the locking means extended to expose the pointed tip of the suture needle.

FIG. 2 depicts the surgical suturing apparatus in side view, with the locking means extended.

FIG. 3 shows the surgical suturing apparatus with the locking means retracted so that the locking member covers the pointed tip of the suture needle; the suture lead is also depicted.

FIGS. 4(a)–(f) provide a detailed illustration of the locking member in three-views: (a) side view; (b) distal view; (c) proximal view; (d) cross-sectional view along D–D' in (a); (e) cross-sectional view along D–D' in (a) for larger locking member; (f) proximal view showing embodiment having a channel in the second bore.

FIG. 5 illustrates an alternate embodiment of the surgical suturing apparatus, wherein the grasping means comprise finger holes and the tubular sheath also comprises finger holes.

FIG. 6 is a partial cross-sectional view of an abdominal section illustrating by way of example tissue layers from the skin to the abdominal wall.

FIG. 7(a)–(h) depict pertinent steps in a method of surgical suturing.

FIG. 8 illustrates a conventional cutaneous closure method.

FIGS. 9(a)–(h) depict pertinent steps in a method of surgical suturing that maintains elevated gas pressure within a body cavity.

FIG. 10a illustrates two incisions open; FIGS. 10b and 10c show suture material having been used to engage two sides of the first incision and the second incision, respectively; FIGS. 10d and 10e show the two incisions having been closed.

FIG. 11 illustrates another embodiment of the surgical suturing apparatus in side view, with the second straight section flared away from the first straight section.

FIGS. 13(a)–(j) depict pertinent steps in a method of suturing a blood vessel sectioned by the insertion of a trocar.

DETAILED DESCRIPTION OF THE PREFERRED EMBODIMENT

The Surgical Suturing Apparatus

Figure 10:
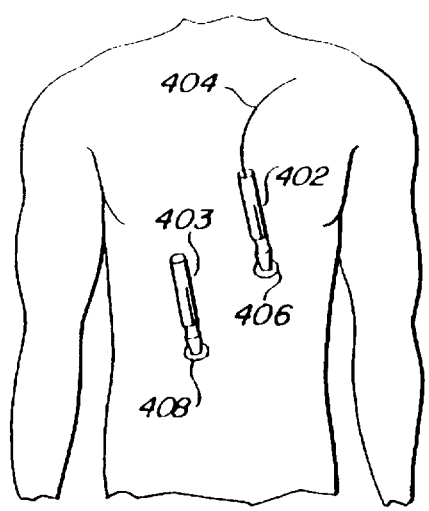
FIGS. 10a–e illustrate a method for suturing multiple incisions.
Figure 10:
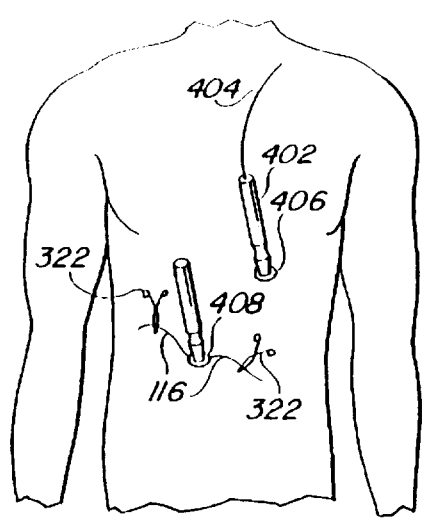
Figure 10:
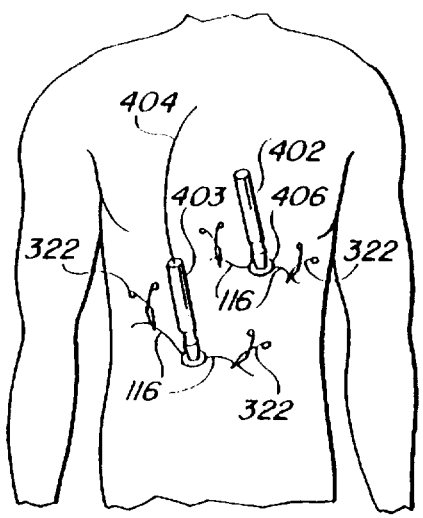
Figure 10:
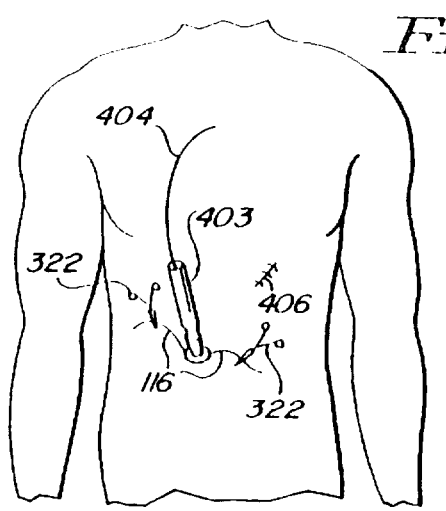
Figure 10:
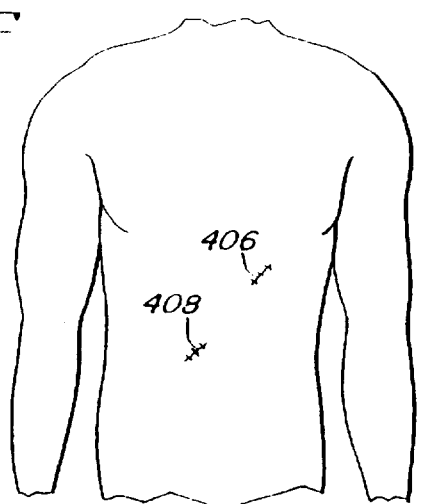

The preferred embodiment of the invention, a surgical suturing apparatus 10, useful in suturing stab wounds or narrow incisions as in the incision created by a trocar used in a laparoscopic or endoscopic surgical procedure, will be discussed. As illustrated in FIGS. 1–3, the preferred embodiment of the invention comprises a needle 130 affixed at its proximal end 131 to a tubular body 102. A tubular sheath 150 and locking member 170 slidingly engage suture needle 130 and are capable of assuming a plurality of positions therealong.

Tubular body 102, of a generally cylindrical shape, comprises an inner surface 112 and outer surface 110. The first, distal end 109 of tubular body 102 comprises a hole 106 dimensioned to permit suture material to pass therethrough and affixing means 103 into which suture needle 130 is inserted. Distal end 109 in the preferred embodiment further comprises at least one arcuate recess 107 dimensioned to engage human fingers and thus facilitate holding the instrument.

The second, proximal end 105 of tubular body 102 comprises a hole 104 dimensioned to permit suture material to pass therethrough and affixing means 101 for the attachment of suture thread holding means 114.

In the embodiment shown in FIGS. 1 and 2, suture thread holding means 114 comprises a spool 118 rotatably affixed to shaft 120. The hollow case 126 of suture thread holding means 114 covers spool 118 and, by means of elongated hollow protrusion 124, slidingly engages the proximal end 105 of tubular body 102. Suture material 116 is wound around spool 118. In one embodiment, spool 118 and case 126 may comprise a commercially available unit, such as the Ligapak (Ethicon, Somerville, N.J.).

Suture needle 130, having a first, proximal end 131 and a second, distal end 136, is affixed at its proximal end 131 to the distal end 109 of tubular body 102 via affixing means 103. The suture needle 130 has a bore 133 dimensioned to permit suture material to pass therethrough. The shape of suture needle 130 comprises a "deep J," having two substantially parallel straight sections 132 and 137 each adjacent a corresponding one of the ends 131 and 136. Second straight section 137 is substantially shorter than first straight section 132. Between the first 132 and second 137 straight sections is curved middle section 134, the three sections 132, 134, and 137 forming a generally "U"-shaped structure. At the end of the second straight section 137 is pointed tip 140, and adjacent pointed tip 140 is suture gate 138, dimensioned to permit suture material to pass therethrough and positioned to communicate with bore 133. The "U"-shaped structure has a center-to-center distance 131 between the bores in the first 132 and second 137 straight sections. The "U"-shaped structure further has an enclosed width 135 defined by the distance between the outer edges of the first 132 and second 137 straight sections of suture needle 130. A first length 139 is defined as the distance between the proximal end 131 of suture needle 130 and pointed tip 140, the distance being measured parallel to first straight section 132.

Suture material 116, having a proximal end 1161 and a distal end 1162, is threaded through the apparatus 10 as follows. Proximal end 1161, as mentioned, is wound around the spool 118 of suture thread holding means 114, from where it issues through hole 104 in the second end 105 of tubular body 102. After proceeding through tubular body 102, suture material 116 issues from hole 106 in the first end 109 in tubular body 102 and enters bore 133 in suture needle 130. Ultimately the distal end 1162 of suture material 116 emerges from suture gate 138.

In another embodiment, no suture thread holding means are used, and the proximal end of suture material 116, which comprises monofilament suture thread, emerges from the proximal end 105 of tubular body 102 through hole 104.

In a further embodiment, shown in FIG. 3, the device is provided with a suture lead 119 having a proximal end 115 and a distal end 117. Suture lead 119 is threaded in the same fashion as suture material through the device. At the distal end 117 is tab 1170, dimensioned larger than suture gate 138, and at the proximal end 115 is split end 1150. In use the operator chooses a suture material 116 having a proximal end 1161 and a distal end 1162 and attaches its distal end 1162 to split end 1150. Tab 1170 is then pulled in a distal direction, threading suture material 116 through the device until distal end 1162 emerges from suture gate 138.

Suture locking means 15, which will be described with reference to FIGS. 1–4, comprises slidable tubular sheath 150 and locking member 170.

Slidable tubular sheath 150, having proximal end 153 and distal end 155, comprises a cylindrical member having bore 151 dimensioned to surround the first straight section 132 of suture needle 130. Affixed to the proximal end 153 of tubular sheath 150 is a means for grasping tubular sheath 150. A length 159 encompasses the distance along the long axis of tubular sheath 150 from the proximal end of the grasping means to the distal end 155 of tubular sheath 150.

In one embodiment the grasping means comprises an annulus 154 having a bore 156 communicating with bore 151 in tubular sheath 150, bore 151 dimensioned to surround the first straight section 132 of suture needle 130 to pass therethrough.

In another embodiment, shown in FIG. 5, the grasping means comprises a first grasping member 254. First grasping member 254 is an elongated member comprising a substantially straight middle portion 256, affixed in a generally perpendicular attitude to the proximal end 153 of tubular sheath 150. From the first end 251 of middle portion 256 depends a first substantially circular portion 257, and from the second end 253 depends a second substantially circular portion 258. Circular portions 257 and 258, distal to middle portion 256, are generally coplanar and are dimensioned to permit human fingers to pass therethrough.

The embodiment shown in FIG. 5 further comprises a second grasping member 240 affixed to the distal end 109 of tubular body 102. In similar fashion to first grasping member 254, second grasping member 240 is an elongated member comprising a substantially straight middle portion 244, affixed in a generally perpendicular attitude to the long axis of tubular body 102. From the first end 241 of middle portion 244 depends a first substantially circular portion 246, and from the second end 243 depends a second substantially circular portion 242. Circular portions 246 and 242, proximal to middle portion 244, are generally coplanar and are dimensioned to permit human fingers to pass therethrough.

Returning to the embodiments illustrated in FIGS. 1–3, it can be seen that affixed to the distal end 155 of tubular sheath 150 is the proximal end 173 of locking member 170. In the preferred embodiment, the shape of locking member 170 is important to its function, and will be described in detail with reference to FIG. 4.

In side view, corresponding to a first plane (FIG. 4(a)), one embodiment of locking member 170 has two generally parallel straight sides 179 and 181. Distal end 175, connecting straight sides 179 and 181 at their distal ends, forms a portion curving out toward the distal direction and shaped generally to conform to the shape of the curved middle section 134 of suture needle 130. Proximal end 173 of locking member 170, connecting straight sides 179 and 181 at their proximal ends, has a curved portion 182, sloping out toward the proximal direction, and connecting with straight side 179. Proximal end 173 then has a shoulder portion 177 curving in the proximal direction and ending substantially parallel with straight side 181. Connecting shoulder portion 177 and straight side 181 is proximal face 183, substantially perpendicular to straight side 181. In this first plane, a first width 184 can be defined by the perpendicular distance between straight sides 181 and 179. The locking member 170 also has a first length 171 defined by the perpendicular distance between proximal face 183 and distal end 175. Locking member 170 further has a second length 189 defined by the perpendicular distance between proximal face 183 and the proximal end 1790 of straight side 179.

In a view from the distal direction toward the proximal direction (FIG. 4(b)), locking member 170 can be seen to have a generally elliptical shape, with slot 175 in distal end 175 generally along the major axis of the ellipse.

In a view from the proximal direction toward the distal direction (FIG. 4(c)), locking member 170 can be seen to have bores 172 and 180, to be discussed below, generally disposed along the major axis of the elliptical shape.

A cross-sectional view taken along D–D' in FIG. 4(a), this second plane being generally parallel to straight sides 179 and 181, is shown in FIG. 4(d). The shape of this cross section is also substantially elliptical, with major axis 186 and minor axis 188. Slot 176 is shown at the distal end 175 of locking member 170.

It should be pointed out that the several elliptical cross sections serve to facilitate the locking member's entry into a slitlike incision. The elliptical cross sections also provide an optimum shape for plugging slitlike incisions.

Locking member 170 has a first bore 178, between proximal face 183 and distal end 175, communicating at its proximal end with the distal end of bore 151 of tubular sheath 150. First bore 178 is dimensioned to slidingly engage first straight section 132 of suture needle 130. Locking member 170 further has a second bore 180, parallel to first bore 178, between curved portion 182 of proximal end 173 and distal end 175, dimensioned to slidingly engage second straight section 137 of suture needle 130. In order to accomplish this, center-to-center distance 131 between the bores in first 132 and second 137 straight sections of suture needle 130 must be substantially equal to center-to-center distance 189 between the bores 172 and 180 in locking member 170. Communicating with and bridging bores 178 and 180 is slot 176 in the distal end 175 of locking member 170. Slot 176 is generally shaped to conform to curved middle section 143 of suture needle 130.

When assembled, bore 151 in tubular sheath 150 communicates with bore 178 in locking member 170, and first straight section 132 of suture needle 130 passes through these bores. Second straight section 137 of suture needle 130 passes through bore 180 in locking member 170. Suture locking means 15 may slide along first straight section 132 of suture needle 130, assuming a plurality of positions determined by the pertinent dimensions of suture needle 130 and suture locking means 15. The sum of length 159 of tubular sheath 150 plus second length 189 of locking member 170 is dimensioned to be approximately equal to the first length 139 of suture needle 130. Thus when suture locking means 15 is in a first position (shown in FIG. 3), that is, when grasping means 154 abuts distal end 109 of tubular body 102, locking member 170 covers pointed tip 140 and suture gate 138. When suture locking means 15 is in a second position (shown in FIGS. 1 and 2), that is, when slot 176 in locking member 170 engages curved middle section 134 of suture needle 130, pointed tip 140 and suture gate 138 are exposed.

In another embodiment of the invention, shown in FIG. 4(e), locking member 570 has a cross section along D–D' in FIG. 4(a) that has protrusions 572 and 574 extending away from the first plane and substantially centered between the proximal 573 and distal 575 ends of locking member 570. This embodiment is preferred for use with larger incisions and larger trocars, wherein the protrusions help in keeping elevated gas pressure within a body cavity being sutured.

In another embodiment the suture needle 730, shown in FIG. 11, has first 732 and second 737 straight sections that are not substantially parallel; rather, curved middle portion 734 at distal end 776 forms a generally parabolic shape, causing first 732 and second 737 straight sections to flare away from each other. The preferred range of angles is 10–40 degrees. This flared geometry permits the surgeon to form wider sutures, since the greatest possible width of a suture is determined by the distance 736 between the first straight section 732 and the pointed tip 740. This flare also gives the surgeon wider latitude when suturing through a trocar or cannula, as will be discussed in the Methods sections. In this embodiment, locking member 770, when in the second position, permits the second straight section 737 to flare away from the first straight section 732, to the degree to which it is biased by its construction. However, when locking member 770 is in the first position, first 732 and second 737 straight sections are brought into a substantially parallel relationship. In this position passage through incisions, cannulas, and trocars is facilitated since the cross-sectional area of the object being inserted is minimized.

A further embodiment of the locking member, shown in FIG. 4(f), the second bore 672 of locking member 670 further has a channel 673 communicating with the suture gate 138. Channel 673 is dimensioned to permit suture material to lie therein, so that suture material emerging from the suture gate 138 may reside in channel 673 when locking member 670 is in the second position, covering suture gate 138.

In the embodiment of the device 10 illustrated in FIG. 1, tubular body 102 and locking member 170 further comprise indicia in the form of dots 98 and 96, respectively. These dots 98 and 96 serve to indicate to the surgeon the orientation of the pointed tip 140 of the suture needle 130. Thus from outside the body cavity being sutured the surgeon can ascertain in which direction the tip 140 is pointing.

Figure 14:
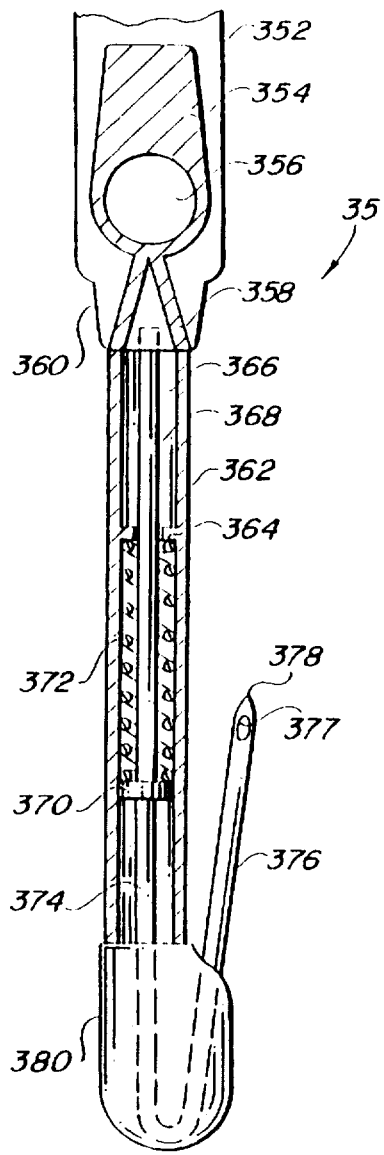
FIG. 14 illustrates an embodiment of the surgical suturing apparatus for use with one hand, the suture locking means being spring loaded.

Another embodiment of the device, shown in FIG. 14, permits one-handed operation. The surgical suturing apparatus 35 contains spring means whereby suture locking means is biased to reside in the first position, with locking member 380 covering suture gate 377 and pointed tip 378. The device 35 further comprises actuating means that communicate with and operate upon the spring means in order to move the suture locking means. In this embodiment tubular body 352 comprises slidable member 354 having a hole 356 dimensioned to permit a human finger to pass therethrough. Slidable member 354 communicates with tubular sheath 362, upon whose inner wall is ridge 364. Suture needle 368, attached at its proximal end to the distal end 360 of tubular body 352, is surrounded by tubular sheath 362. Suture needle 368 further comprises a ridge 370 positioned distal of ridge 364. Spring 372 fits between a portion of the first straight section of suture needle 368 and the interior surface of tubular sheath 362, residing between ridges 370 and 364, such that a movement of slidable member 354 in a distal direction compresses spring 372 at the same time that is moves tubular sheath 362 in a distal direction. Thus, in an unstressed condition, spring 372 will tend to move tubular sheath 362 in a proximal direction, with the result that locking member 380 covers suture gate 377 and pointed tip 378.

Figure 12A:
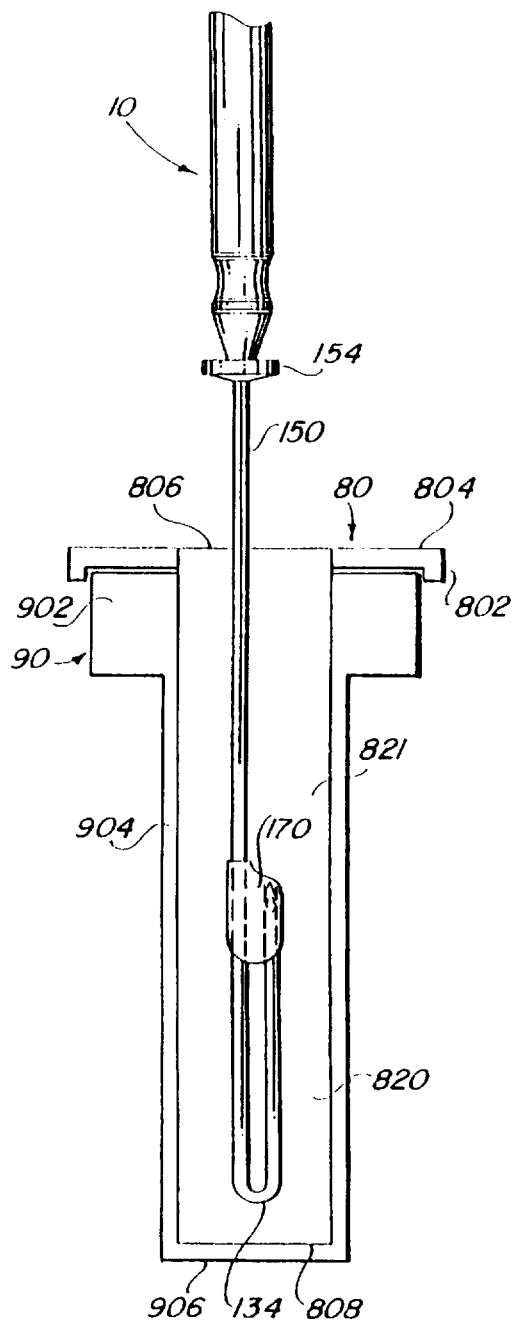
FIG. 12(a) is a cross-sectional view of the surgical suturing apparatus placed within a sealed cannula, the cannula in turn placed within a trocar; (b) top view of the diaphragm that seals the proximal end of the cannula; (c) top view of the diaphragm that seals the distal end of the cannula.
Figure 12B:
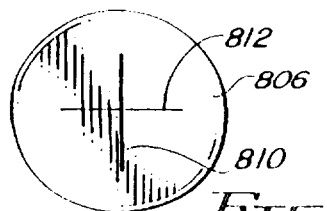
Figure 12C:
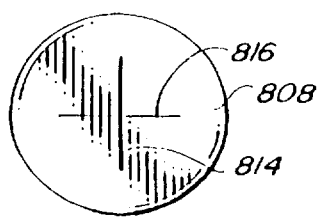

FIG. 12 illustrates an embodiment in which the surgical suturing apparatus further comprises a cylindrical cannula member that surrounds the distal end of the suture needle. In this embodiment, which is useful in procedures in which it is desired to maintain elevated gas pressure within a body cavity during suturing, cannula 820 has an inner space 821 dimensioned to permit the suture needle and suture locking means to pass therethrough. At the proximal and distal ends of cannula 820 are proximal 806 and distal 808 diaphragms, respectively. Proximal diaphragm 806 has two substantially perpendicular slits 810 and 812, dimensioned to permit the suture needle and suture locking means to pass therethrough and sealingly surround the suture needle and tubular sheath to form a substantially airtight seal. Distal diaphragm 808 likewise has two substantially perpendicular slits 814 and 816 similarly dimensioned and constructed.

In yet another embodiment, also illustrated in FIG. 12, the proximal end of cannula 820 further comprises means 80 for sealingly engaging the proximal end 902 of trocar 90. In this embodiment cannula 820 is dimensioned to fit inside trocar 90, which has a distal aperture 906. The sealing means 80 in FIG. 12 take the form of an annular diaphragm 804 and lip 802 dimensioned to sealingly surround the aperture at the proximal end 902 of trocar 90 and to sealingly engage diaphragm 806.

Method of Suturing a Narrow Incision in a Subcutaneous Tissue Layer

The above-disclosed apparatus 10 may be used in any laparoscopic or endoscopic application. For purposes of illustration, however, its use will be described for suturing a small incision associated with a trocar puncture in the abdomen.

With reference to FIG. 6, it can be seen that the abdominal wall 66 comprises the peritoneum 68, a layer of muscle tissue 70, and the cutaneous layer 72. The subcutaneous fat 74 layer is not sutured.

The method for utilizing the above-disclosed apparatus 10 for suturing a narrow incision 300 will now be described with reference to FIG. 7. Incision 300 comprises an incision 301 in the-cutaneous layer 304 and at least one incision 302 in a subcutaneous layer 310. In two-handed use, tubular body 102 is held in the surgeon's nondominant hand, and grasping member 154, forceps 320, and securing device 322 are manipulated with the dominant hand.

With the tubular sheath 150 in the first position, that is, with the pointed tip 140 and suture gate 138 covered with locking member 170, the distal end 136 of suture needle 130 is inserted into the incision 300 sufficiently deep that the pointed tip 140 of suture needle 130 is beneath one side 312 of the deepest layer of tissue 310 to be sutured (FIG. 7(a)). The tubular sheath 150 is then slid into the second position, exposing the pointed tip 140 and suture gate 138. The pointed tip 140 is then brought surfaceward through a first side 312 of the tissue layer 310 sufficiently far to pull the distal end 1162 of the suture material 116 through first side 312, penetrating only one layer of tissue (FIG. 7(b)).

Using forceps 320 or other suture material grasping means, the suture material 116 is brought out of the incision 300 to a length sufficient for tying a knot and is then secured, for instance, with a clamping means such as a hemostat 322 (FIG. 7(c)).

The suture needle 130 is then pushed back into the incision 300, again sufficiently deep that the pointed tip 140 is beneath the deepest layer 310 of tissue to be sutured. The suture needle 130 is then rotated, so that the pointed tip 140 is positioned beneath a second side 314 of tissue 310 (FIG. 7(d)). Suture needle 130 is then brought surfaceward once more, bringing the pointed tip 140 and suture gate 138 through second layer 314 (FIG. 7(e)).

Using the forceps 320 again, the suture material 116 is grasped at the suture gate 138 and pulled out of the incision 300 to a length sufficient for tying a knot (FIG. 7(f)). The tubular sheath 150 is returned to the first position, locking the suture material 116 against the suture gate 138. The suture material 116 is then cut at the point of being grasped by the forceps 320, the suture needle 130 is withdrawn from the incision 300 (FIG. 7(g)), and a knot is tied (FIG. 7(h)).

This procedure may be repeated on the same layer of tissue to form multiple sutures, such as in the form of an "X" or a plurality of parallel sutures.

The procedure may also be repeated on successively more shallow layers of tissue until all but the cutaneous layer are closed, the final step of the closure comprising suturing the cutaneous layer by conventional means, such as shown in FIG. 8. Such a conventional closure of incision 301 in cutaneous layer 304 may comprise, for instance, making multiple surface sutures 340 along incision 301 with the use of suture needle 88, suture material 116, and forceps 320.

Methods for Suturing Narrow Incisions while Maintaining Gas Pressure within a Body Cavity Method 1

The apparatus depicted in FIGS. 1–3 is useful in another embodiment for suturing narrow incisions in body cavities and at the same time maintaining an elevated gas pressure within the cavity. Since suturing entails entering the incision a number of times, conventional methods can cause a loss of pressure each time the suture needle spreads the sides of the incision apart.

Device 10 permits performing a suturing operation in a subcutaneous layer 310 while maintaining gas pressure, as will be shown with reference to FIG. 9.

As in the previously described method, incision 300 comprises an incision 301 in the cutaneous layer 304 and at least one incision 302 in a subcutaneous layer 310. In two-handed use, tubular body 102 is held in the surgeon's nondominant hand, and grasping member 154, forceps 320, and securing device 322 are manipulated with the dominant hand.

With the tubular sheath 150 in the first position, that is, with the pointed tip 140 and suture gate 138 covered with locking member 170, the distal end 136 of suture needle 130 is inserted into the incision 300 sufficiently deep that the pointed tip 140 of suture needle 130 is beneath one side 312 of the deepest layer of tissue 310 to be sutured (FIG. 9(a)). Tubular body 102 is then pulled surfaceward sufficiently far that locking member 170 plugs incision 302.

It can be seen that the shape of locking member 170 is optimal for this function, since incision 302 has a roughly slitlike shape. As noted with reference to FIGS. 4(b)–(d), locking member has elliptical cross sections in two planes: the plane normal to the suture needle and the plane parallel to that formed by the two straight sections 137 and 132 of needle 130. These elliptical cross sections facilitate the locking member's entry into and removal from an incision, and also provide an effective shape for plugging a slit-shaped incision.

To continue with the suturing method, tubular sheath 150 is maintained via grasping member 154 in a stationary position to retain the position of locking member 170 within incision 302, while at the same time tubular body 102 is pulled surfaceward out of incision 300. This action moves suture needle 130 relative to tubular sheath 150 to expose needle tip 140, which is pulled through the first side 312 of tissue 310 to be sutured. When tubular sheath 150 has been moved into the second position, exposing the pointed tip 140 and suture gate 138, the distal end 1162 of the suture material 116 has penetrated first side 312 (FIG. 9(b)).

Using forceps 320 or other suture material grasping means, the suture material 116 is brought out of the incision 300 to a length sufficient for tying a knot and is then secured, for instance, with a clamping means such as a hemostat 322 (FIG. 9(c)).

Still maintaining locking member 170 within incision 302 by holding grasping member 154 stationary relative to incision 300, suture needle 130 is then pushed back into the incision 300, again sufficiently deep that the pointed tip 140 is beneath the deepest layer 310 of tissue to be sutured. The suture needle 130 is then rotated, so that the pointed tip 140 is positioned beneath a second side 314 of tissue 310 (FIG. 9(d)). Suture needle 130 is then brought surfaceward once more, still maintaining locking member 170 within incision 302, bringing the pointed tip 140 and suture gate 138 through second layer 314 (FIG. 9(e)).

Using the forceps 320 again, the suture material 116 is grasped at the suture gate 138 and pulled out of the incision 300 to a length sufficient for tying a knot (FIG. 9(f)). The suture material 116 is then cut at the point of being grasped by the forceps 320, the suture needle 130 is withdrawn from the incision 300 (FIG. 9(g)), and a knot is tied (FIG. 9(h)).

Method 2

Another embodiment of the method utilizes the apparatus having a cannula surrounding the suture needle (FIG. 12). In this embodiment the cannula is inserted into the incision, the diaphragms serving to maintain gas pressure within the body cavity. The suture needle is pushed into the cannula and then into the incision sufficiently deep so that the second straight section of the suture needle is distal of the cannula. The pointed tip is then moved beneath the tissue layer to be sutured and brought toward the surface through a first side of the incision sufficiently far to pull the suture gate through the first side of the incision. Using forceps or like grasping means, the distal end of the suture material is grasped and pulled out of the incision to a length sufficient for tying a knot.

This procedure is repeated for the second side of the incision, the suture material is cut, the suture needle and cannula are removed from the incision, and a knot is tied.

Method 3

A third embodiment of the method entails the use of the apparatus comprising a cannula having means for engaging a trocar (FIG. 12). This method is identical to Method 2, with the exception that the cannula and suture needle are inserted into a trocar already residing within an incision, with the distal end of the cannula protruding into the incision farther that the distal end of the trocar, so that the suture material is not cut by the trocar's sharp distal edge.

Method for Suturing a Plurality of Narrow Incisions

Apparatus 10 may also be utilized in suturing multiple incisions, such as those incurred during laparoscopic procedures in which visualizing means are inserted through one of a plurality of trocars.

A method for suturing multiple incisions while maintaining visualization ability for all suturing procedures will be described with reference to FIGS. 10a–10e.

If the operation has caused the introduction of more than two incisions, all but two should be closed with the use of one of the methods described above. The first of the two remaining should be the incision 406 through which the trocar 402 carrying the visualizing means 404 has been inserted. The second 408 should be chosen for ease of visualization from the site of the first incision 406.

FIG. 10(a) illustrates the situation wherein two incisions 406 and 408 remain open in the peritoneum. Utilizing one of the methods described above, with the aid of visualizing means 404, incision 408 is sutured, but not closed. That is, the procedure is carried out to the point at which two ends of suture material have engaged the two sides of a subcutaneous incision and have been secured with clamping means 322 and the suture needle has been removed (FIG. 9(g); FIG. 10(b)).

The next step comprises removing trocar 402 and visualizing means 404 from incision 406 and inserting them into incision 408, avoiding displacing suture material 116. Incision 406 may now be completely sutured with the use of one of the above-described methods and the visualizing means 404 (FIG. 10(c)). Conventional means such as that shown in FIG. 8 may be used to close the cutaneous layer.

The final portion of the method comprises removing trocar 402 and visualizing means 404 from incision 408 and tying a knot in the suture material already in place in incision 408, and closing the cutaneous layer (FIG. 10(*d*)).

Method for Suturing a Severed Blood Vessel Adjacent a Cannula

During laparoscopic or endoscopic surgical procedures, it may happen that a blood vessel is inadvertently severed by the insertion of the trocar, which are cannulas having sharp distal edges. A method is presented here for the suturing of the ends of the blood vessels without removing the trocar, as illustrated in FIG. 13. The blood vessel is assumed to be adjacent a subcutaneous layer of tissue, through which the trocar also passes.

Utilizing the surgical suturing apparatus disclosed above, the suture needle is inserted into the trocar sufficiently deep that the pointed tip is beneath the distal end of the cannula [FIGS. 13(*a*) and (*b*)]. The pointed tip is then positioned beneath a first side of the severed blood vessel and also beneath the adjacent subcutaneous layer of tissue and then brought surfaceward through the tissue sufficiently far to pull the suture gate through the tissue layer [FIGS. 13(*c*) and (*d*)]. The distal end of the suture material is then grasped by forceps or other suitable grasping means and pulled out of the incision to a length sufficient for tying a knot.

The suture needle is then reinserted into the incision sufficiently deep that the pointed tip is beneath a second side of the severed blood vessel and beneath the adjacent tissue layer [FIGS. 13(*e*) and (*f*)]. The procedure outlined above is repeated [FIGS. 13(*g*) and (*h*)], the suture material is cut, and a knot is tied [FIGS. 13(*i*) and (*j*)].

The suture needle is next reinserted into the incision, and the entire process is repeated for the second severed end of the blood vessel, after which the suture needle is removed from the cannula.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of the preferred embodiment thereof, and the advantageous new and useful results obtained thereby, the new and useful constructions, and reasonable mechanical equivalents thereof obvious to those skilled in the art, are set forth in the appended claims.

What is claimed is:

1. A locking member for use in an endoscopic surgical procedure for maintaining gas pressure within a body cavity having an incision thereinto, the locking member slidably affixable in surrounding relation to an end of a suture needle affixed to a manipulator for movement relative to the incision and comprising a unitary member having a generally rounded distal end and a smooth outer contour for ease of entry into and withdrawal from the incision, the unitary member shaped commensurate with and sufficiently large to plug the incision against release of gas pressure the locking member having:

a distal end;

a proximal end;

a cross-sectional shape in a first plane, the first plane including the distal and the proximal ends, the first plane cross-sectional shape comprising an outwardly curving section at the distal end connecting with two generally parallel, generally straight sides;

a generally elliptical cross-sectional shape in a second plane generally normal to the isdes and generally perpendicular to the first plane, the sides defining ends of a major elliptical axis; and a protrusion in a third plane generally normal to the sides and generally perpendicular to the first plane and the second plane, the protrusion for plugging the incision against leakage of gas pressure from the body cavity.

\* \* \* \* \*